United States Patent [19]

Becwar et al.

[11] Patent Number: 5,610,051
[45] Date of Patent: Mar. 11, 1997

[54] METHOD FOR PRODUCTION OF CONIFEROUS ISOGENIC CELL LINES

[75] Inventors: Michael R. Becwar; Thomas D. Blush, both of Summerville, S.C.

[73] Assignee: Westvaco Corporation, New York, N.Y.

[21] Appl. No.: 717,042

[22] Filed: Jun. 18, 1991

[51] Int. Cl.⁶ .............................. C12N 1/20; C12N 3/00; C12N 5/00

[52] U.S. Cl. ...................... 435/422; 435/242; 435/252.4; 435/6

[58] Field of Search .......................... 435/240.1, 252.4, 435/240.4, 240.54, 242

[56] References Cited

U.S. PATENT DOCUMENTS

| | | | |
|---|---|---|---|
| 4,957,866 | 9/1990 | Gupta et al. | 435/240.48 |
| 5,034,326 | 7/1991 | Pullman et al. | 435/240.4 |
| 5,041,382 | 8/1991 | Gupta et al. | 435/240.47 |

*Primary Examiner*—Michael G. Wityshyn
*Assistant Examiner*—Deborah K. Ware
*Attorney, Agent, or Firm*—Daniel B. Reece, IV; Terry B. McDaniel; Richard L. Schmalz

[57] ABSTRACT

This invention relates to the production of genetically homogeneous cell lines from coniferous plants. In particular, this invention describes a method for producing isogenic cell lines of embryogenic cultures derived from immature conifer seeds. This method is suited for producing clonal planting stock useful for reforestation.

8 Claims, 6 Drawing Sheets

Dominant zygotic embryo

Extrusion of polyembronic and embryogenic tissue

METHOD FOR PRODUCTION OF CONIFEROUS ISOGENIC CELL LINES

FIELD OF INVENTION

This invention relates to the production of genetically homogeneous cell lines from coniferous plants. In particular, this invention describes a method for producing isogenic cell lines of embryogenic cultures derived from immature conifer seeds. This method is suited for producing clonal planting stock useful for reforestation.

BACKGROUND OF THE INVENTION

Southern pines (Pinus) (i.e., loblolly pine, slash pine, etc.) and Douglas-fir (*Pseudotsuga menziesii*) are among the most important commercial species of North American timber trees. Due to the voracious demands of the lumber and paper industries, literally billions of these trees have been harvested and replanted since the early 1940's, when the first serious private reforestation efforts were initiated.

As is true with most crops, trees have been selected and manipulated by man in order to promote certain desired characteristics; such as rapid growth, resistance to insects and disease, straightness of bole, fiber length, wood density, and so on. Currently, in both the southern pine and Douglas-fir regions the majority of the seed utilized in reforestation efforts is produced from selected trees grown in seed orchards.

Although these seed orchards contain superior trees, it is extremely difficult to strictly control the pollination of the trees. Often the seed trees are fertilized by wild pollen from unselected trees. This problem can result in sexually reproduced progeny with less genetic gain potential than could have been obtained if the seed orchard trees had been fertilized by pollen from other genetically superior trees.

One method traditionally used by geneticists to solve this problem of wild pollination generating inferior genotypes is to reproduce the plant in the laboratory via tissue culture. However, forest tree species have proven difficult to reproduce in this manner. It was not until the late 1970's that Douglas-fir and loblolly pine were successfully reproduced via tissue culture. An excellent history of the development of this type of reproduction (as well as a method for reproducing coniferous plants by somatic embryogenesis) is provided by U.S. Pat. No. 4,957,866 to Gupta et al., which is hereby incorporated by reference.

Despite recent advances in procedures for laboratory reproduction of coniferous plants, a major problem remains for those researchers attempting to produce isogenic (single genotype) cell lines. Multiple zygotic embryos may form in conifer seeds due to polyembryony (Singh, 1978). Cleavage polyembryony is the division or cleavage of early stage embryos into four embryos. Cleavage embryos are genetically identical to the zygotic embryo from which they are derived. The other form of polyembryony, simple polyembryony, is due to multiple fertilization events within an individual conifer seed. It is very common for conifer seeds to have more than one egg cell per seed (Allen and Owens, 1972). Therefore, the potential exists for simple polyembryony in conifer seeds. During pollination it is also common for several male pollen grains (each is genetically different) to make their way into the seed. As a result, multiple fertilization events can occur within an individual seed. Unlike the cleavage embryos, embryos derived from different fertilization events are genetically different from each other.

As an example, if a single conifer seed contains three egg cells that are fertilized via pollen from different trees (FIG. 1) and the resulting three zygotic embryos undergo cleavage (where each divides into four embryos) (FIG. 2), then the seed would contain 12 developing embryos with three different genotypes (FIG. 3). In most conifers, as the seed matures, one embryo dominates and the other embryos fail to develop fully and eventually lose viability.

With several species of conifers, embryogenic cell cultures which can regenerate plants via somatic embryogenesis are established by culturing the entire seed (with the seed coat removed) which contains the developing immature embryos (Gupta and Durzan, 1987; Becwar et al., 1988; Finer et al., 1989; Becwar et al., 1990). The optimum stage for initiating the cultures from pine seeds is when the multiple embryos, due to simple and cleavage polyembryony, are still viable (Becwar et al., 1990; Finer et al., 1989). It is possible to initiate embryogenic cultures from more than one of the multiple zygotic embryos.

Embryogenic cultures which originate from seeds with multiple zygotic embryos, therefore, may be genetic mosaics (i.e., cultures with multiple genotypes). The possibility of having embryogenic cultures which are multigenic poses a serious limitation to the application of somatic embryogenesis to clonal forestry. In order to regenerate clonal planting stock from embryogenic cultures, it will be necessary to have isogenic cell lines. This will ensure that all of the plants regenerated from one cell line are genetically equivalent.

A common assumption (or misconception) is that explant tissues used for initiation of embryogenic conifer cultures are isogenic. In fact, for the reasons mentioned above, this may not be the case when cultures are initiated from immature conifer seeds which contain the polyembryonic tissues.

The most obvious way that the problem can be alleviated is to start with explant tissue that is known to be of a single genotype. For instance, by starting with mature zygotic embryos (since in most conifers the secondary zygotic embryos quickly loose viability as the dominant embryo matures) or isolated parts of mature zygotic embryos of conifers, one can obtain an embryogenic culture derived from solely one genotype. It is possible to do so routinely with conifers in the Picea (spruce) genus (Attree et al., 1991), but it has been much more difficult to do with conifers in the Pinus (pine) genus. Only one report (Gupta and Durzan, 1986) has claimed to initiate embryogenic cultures from mature zygotic embryos of pines, and this work has not been duplicated or repeated by other workers.

Therefore, to initiate embryogenic cultures capable of regenerating plants in several genera of conifers [including the economically important genera Pinus, Pseudotsuga (Douglas-fir), and Larix (Larch)], the only alternative is to start with zygotic embryos derived from immature seeds. One way to do so is to isolate the dominant immature zygotic embryo from the seed and culture it individually. This has worked in several species (e.g.; spruce, pine, and larch), but it is exceedingly tedious and culture initiation frequencies are lower than when the entire seed is cultured (Finer et al., 1989). Furthermore, it is difficult to ensure that one is only getting a single isolated zygotic embryo due to polyembryony and the small size of the embryos within the seed.

An alternative to isolating individual immature zygotic embryos has worked with several conifer species. With this technique, the immature seed (with the seed coat, nucellus, and megaspore wall tissues removed) which contains the developing zygotic embryos is cultured. Thus, the zygotic embryos are cultured intact within the surrounding nutritive tissue of the seed (the megagametophyte). This technique was first used with Radiata pine and since has proven effective on numerous other species (Gupta and Durzan, 1987; Becwar et al., 1988; Finer et al., 1989; Becwar et al., 1990; Norgaard and Krogstrup, 1991). Using this technique, zygotic embryos and embryogenic tissue are extruded out of the megagametophyte onto the culture medium. The extruded tissue is comprised of individual embryos (zygotic and/or somatic embryos) and individual or aggregates of suspensor cells. The embryogenic tissue proliferates from the zygotic embryos, and by transfer to an appropriate medium, further development of the somatic embryos can be induced and plants regenerated.

Other researchers have used a slight modification of the above technique where the culture is of a section of the megagametophyte (usually a transverse section) which contains the early stage zygotic polyembryonic tissue. This has proven effective for initiating embryogenic cultures of Douglas-fir (Durzan and Gupta, 1987), *Abies alba* (Schuller et al., 1989), and *Larix* species (Klimaszewska, 1989).

However, the above methods of initiating embryogenic cultures in conifers by culturing seed tissue or sections of seed tissue which contains multiple and genetically different zygotic embryos have a major limitation when used for clonal forestry. Namely, due to simple polyembryony, the extruded embryogenic tissue may be genetically heterogeneous—a genetic mosaic. Thus, somatic embryos and plants regenerated from such multigenic cultures may be genetically heterogeneous. This can cause great problems for genetic researchers attempting to produce pure genetic strains of superior stock via somatic embryogenesis for the purpose of cloning.

Therefore, it is the object of this invention to provide a process for producing isogenic cell lines of embryogenic conifer cultures. Other objects, features, and advantages will be evident from the following disclosure.

SUMMARY OF THE INVENTION

The object of this invention is met by culturing immature seeds of conifers (specifically, the megagametophyte containing developing immature zygotic embryos) to obtain isogenic cell lines from the explant. In particular, the key step in the invention is the isolation of individual embryos immediately after they have extruded from the megagametophyte, and the subsequent establishment of cell lines from these isolated embryos. As these subsequently established cell lines are from individual embryos, the cell lines will be isogenic. It is the addition of this step (i.e., isolating the extruded embryos) in our invention that improves on the previously mentioned procedures and thereby alleviates a potential for multigenic cell lines. The cell lines may then be genetically evaluated by any number of known techniques (e.g., DNA, isozyme or protein, genetic marker, morphological, etc.) for a variety of purposes.

There are several advantages inherent with the use of this novel process. The process is more efficient than isolating individual zygotic embryos prior to extrusion and culturing them individually. That is, if one were to attempt to isolate individual zygotic embryos before the extrusion event, it can not be determined which embryos are subsequently going to extrude from the seed and proliferate to form an embryogenic culture. Therefore, one would need to isolate many more individual zygotic embryos in order to ensure that responsive embryos are obtained which will proliferate to form embryogenic tissue.

Thus, this process utilizes the extrusion event in order to selectively isolate embryos that have already shown potential for proliferation. In addition, after the extrusion event it is also much easier to isolate individual embryos from the extruded embryogenic tissue (which is now easily accessible outside of the confinement of the megagametophyte tissue). By contrast, it is much more difficult to excise zygotic embryos prior to the extrusion event from within the corrosion cavity of the intact megagametophyte.

This novel process also enables one to utilize the most responsive stage of zygotic embryo development in several conifers—just after fertilization—when the zygotic embryos are extremely small and difficult to remove from the seed. Embryogenic cultures of eastern white pine were initiated from zygotic embryos with intact megagametophytes as early as one week after fertilization, with the optimum initiation frequency reached two to three weeks after fertilization (Finer et al., 1989). In this study, by three weeks after fertilization zygotic embryos ranged from 0.1 to 0.3 mm. At this stage of zygotic embryo development it was possible to excise and culture individually the dominant zygotic embryo, but it was not possible to isolate and separately culture smaller secondary zygotic embryos due to their small size. In another study using loblolly pine (Becwar et al., 1990), embryogenic cultures were initiated from zygotic embryos with intact megagametophytes (the time was estimated to be about one week after fertilization). In this study, it was not practical to excise the dominant zygotic embryo out of the megagametophyte (due to their small size) and establish embryogenic cultures until one month later. Other reports have indicated embryogenic cultures of pines were initiated during the very early stages of zygotic embryo development; 4 to 5 weeks after fertilization (Gupta and Durzan, 1987).

Thus, it is apparent that it is possible to obtain embryogenic cultures from very early stage zygotic embryos of several conifers, prior to when it is feasible to efficiently isolate even the largest dominant zygotic embryo (and it is extremely difficult to isolate the smaller secondary zygotic embryos).

This novel process enables one to utilize this early stage of zygotic embryo development for the initial extrusion of embryogenic tissue. It thus avoids having to dissect individual zygotic embryos out of the megagametophyte by relying on the extrusion event to position the embryos outside the megagametophyte for relatively easy isolation.

This novel process also provides a way by which one can obtain (from one seed) multiple cell lines (i.e., the multigenic entities represented by the secondary embryos) that may be genetically different from each other in order to screen for genetic superiority. For the first time one may, by using this process, genetically screen within a single conifer seed.

Likewise, this process provides for the first time a way to determine whether the dominant zygotic embryo is indeed genetically superior relative to the secondary embryos that normally do not survive to maturity. This is accomplished by using the appropriate genetic analysis (e.g., isozyme analysis of controlled crosses made with multiple pollen parents of known marker loci), and by cutting the seed open after extrusion to locate the dominant zygotic embryo. The genotype of the dominant zygotic embryo is then compared to the genotype(s) of the cell lines, somatic embryos, and plants derived from the extruded embryogenic tissue.

This novel process also provides a way to establish at the onset of proliferation that a cell line, somatic embryos, and regenerated plants were derived from a single embryo. It is advantageous to do this as early as possible in order to avoid undue investment of time and resources in maintaining cell lines that later turn out to be genetic mosaics.

BRIEF DESCRIPTION OF THE DRAWINGS

The figures show various stages in the process for the production of isogenic cell lines.

DESCRIPTION OF THE PREFERRED EMBODIMENT

Figure 1:
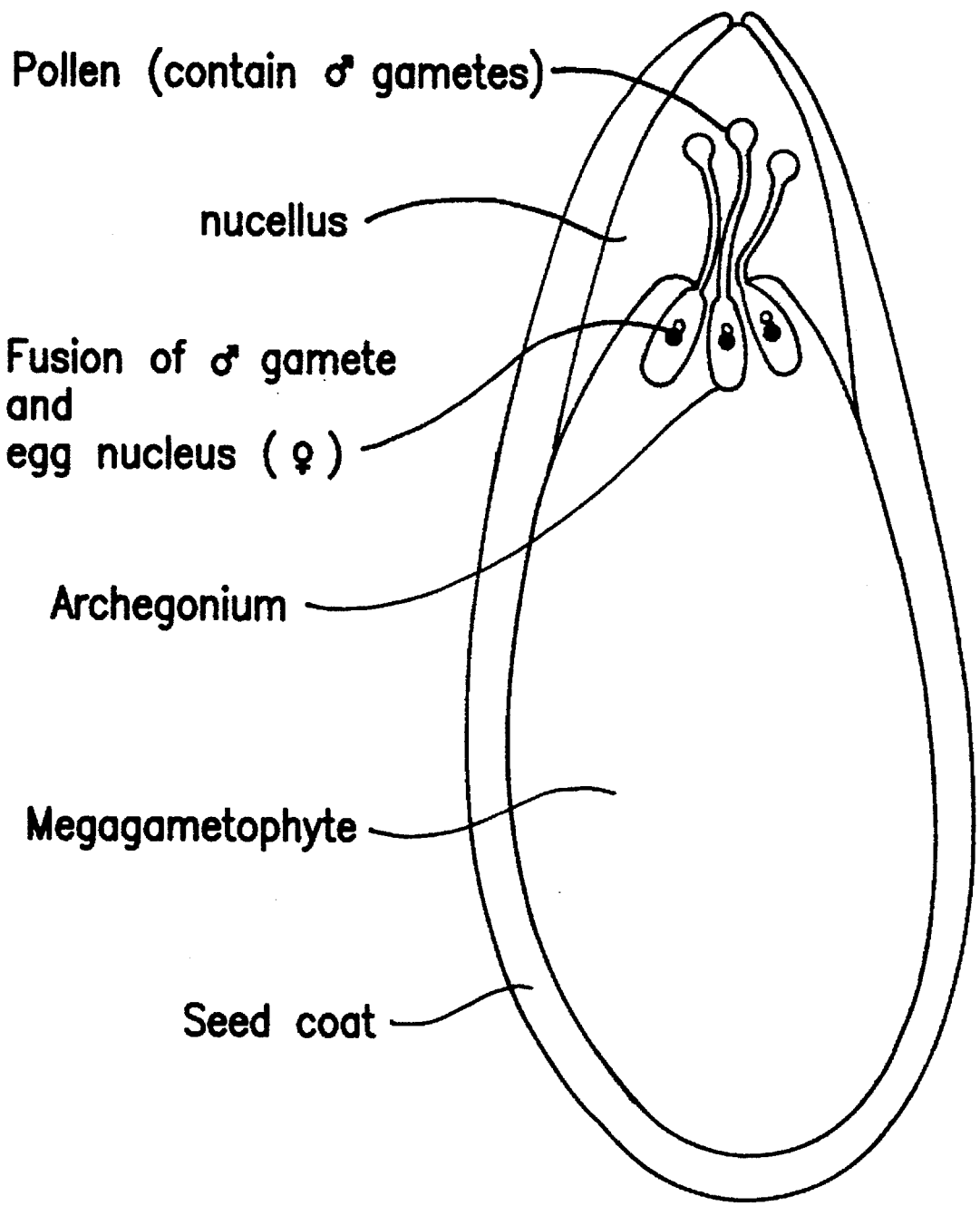
FIG. 1 shows multiple fertilization in conifers. In this example, three pollen grains, each from a different tree, fertilized three egg nuclei within an individual seed. In the figure: A designates the pollen grains (containing male gametes); B designates the nucellus; C designates the fusion of a male gamete and the female egg nucleus; D designates the archegonium; E designates the megagametophyte; and F designates the seed coat.

Conifer embryogenic tissue derived from immature zygotic embryos may consist of multiple genotypes due to simple polyembryony. Our invention teaches a method specifically for producing isogenic cell lines of embryogenic conifer cultures, thereby alleviating a potential for multigenic cell lines.

This method is different from the process known in the art as embryo rescue (Collins and Grosser, 1984). Unlike embryo rescue, it is not the primary purpose of this invention to grow the isolated extruded embryos directly into plants. Instead, one is able to initiate an embryogenic culture with plant regeneration capacity from the isolated embryos which have been extruded from the seed.

Conifer genera which are suitable sources of embryogenic tissue for use in this process include, but are not limited to, the following:

Abies

Chamaecyparis

Cupressus

Juniperus

Larix

Libocedrus

Picea

Pinus

Pseudotsuga

Sequoia

Taxodium

Taxus

Thuja

Torreya

Tsuga.

The process of the present invention is not limited to any single culture medium or to the use of specific plant growth hormones. Any of a number of well known media, such as that of Murashige and Skoog (1962) or modifications thereof, may be used.

It should also be recognized that there is not one single set of culturing conditions that will be suitable for achieving viability of all species or for all genotypes within a species. Tissue culture as a whole is a highly unpredictable science. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture.

A number of terms are known to have differing meanings when used in the literature. The following definitions are believed to be the ones most generally used in the field of botany and are consistent with the usage of the terms in the present specification.

A "cell line" is a culture that arises from an individual explant.

"Corrosion cavity" is the cavity within the megagametophyte tissue of conifers formed by the growth and enlargement of the zygotic embryos.

A "dominant zygotic embryo" is one zygotic embryo among the multiple embryos formed in conifer seeds due to simple and cleavage polyembryony that outgrows the other zygotic embryos and matures in the seed.

"Embryo rescue" is the removal of immature zygotic embryos from the seed and culture in vitro to induce continued development and germination to obtain a plant. This technique is used in angiosperm seeds but has not been effective for conifer seeds. It is used for embryos that fail to develop and abort if left in the seed.

An "embryogenic culture" is a plant cell or tissue culture capable of forming somatic embryos and regenerating plants via somatic embryogenesis.

"Embryogenic tissue", in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well formed somatic embryos, the embryogenic tissue may contain small, dense clusters of cells capable of forming somatic embryos.

An "explant" is the organ, tissue, or cells derived from a plant and cultured in vitro for the purpose of starting a plant tissue culture.

"Extrusion" is the process by which zygotic embryos and/or embryogenic tissue emerges from the corrosion cavity of the megagametophyte of conifer seeds via the opening in the micropylar end, when placed in culture.

"Genotype" is the genetic constitution of an organism; the sum total of the genetic information contained in the chromosomes of an organism.

An "immature conifer seed" is one wherein the embryos have not yet fully developed.

"Initiation" is the initial cellular proliferation or morphogenic development that eventually results in the establishment of a culture from an explant.

"Isogenic" means of any group of individuals (or cells) which possess the same genotype.

"Isozyme" is any of a class of multiple, separable forms of enzymes (=isoenzymes) occurring within the same organism and having similar or identical catalytic activity.

An "isozyme analysis" is the use of isozyme polymorphisms for genetic analysis whereby the different physical properties of the isozymes can serve as genetic markers.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Regeneration", in plant tissue culture, is a morphogenic response to a stimuli that results in the production of organs, embryos, or whole plants.

A "secondary zygotic embryo" is a zygotic embryo formed in conifer seeds due to simple and cleavage polyembryony, that does not develop fully and looses viability as the dominant zygotic embryo matures in the seed.

"Simple polyembryony" is the development of multiple (and genetically dissimilar) embryos within one ovule due to fertilization of more than one egg by different pollen grains.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspensor cell" is an extension of the base of the embryo that physically pushes the embryo into the megagametophyte in conifer seeds and is comprised of elongated and highly vacuolated cells.

A "zygotic embryo" is an embryo(s) which is derived from the sexual fusion of gametic cells.

The following examples are provided to further illustrate the present invention and are not to be construed as limiting the invention in any manner.

EXAMPLE 1

Figure 2:
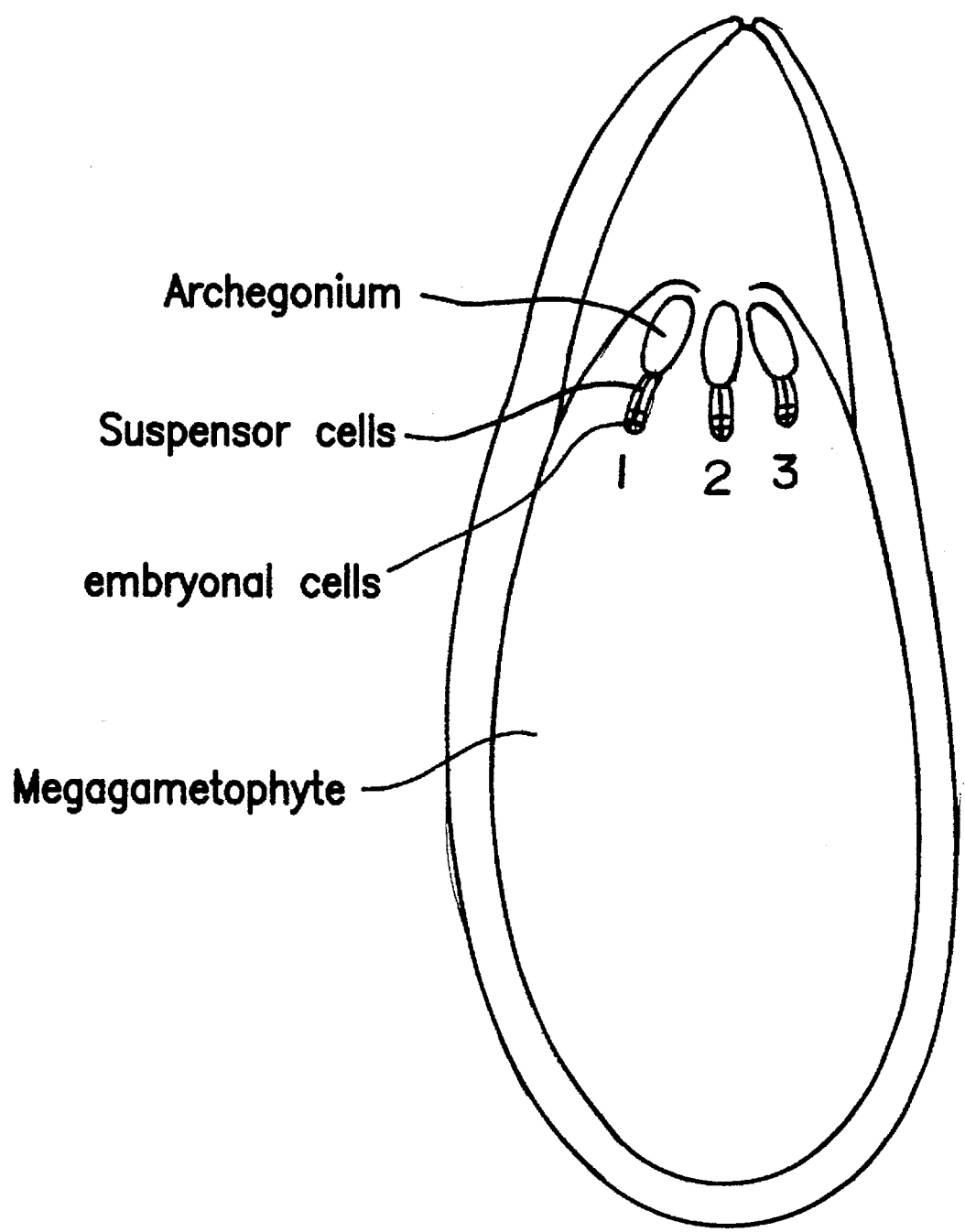
FIG. 2 shows simple polyembryony in conifers. Multiple fertilization results in three genetically different zygotic embryos (genotypes 1, 2, and 3) within an individual seed. In the figure: A designates the archegonium; B designates the suspensor cells; C designates the embryonal cells; and D designates the megagametophyte.
Figure 3:
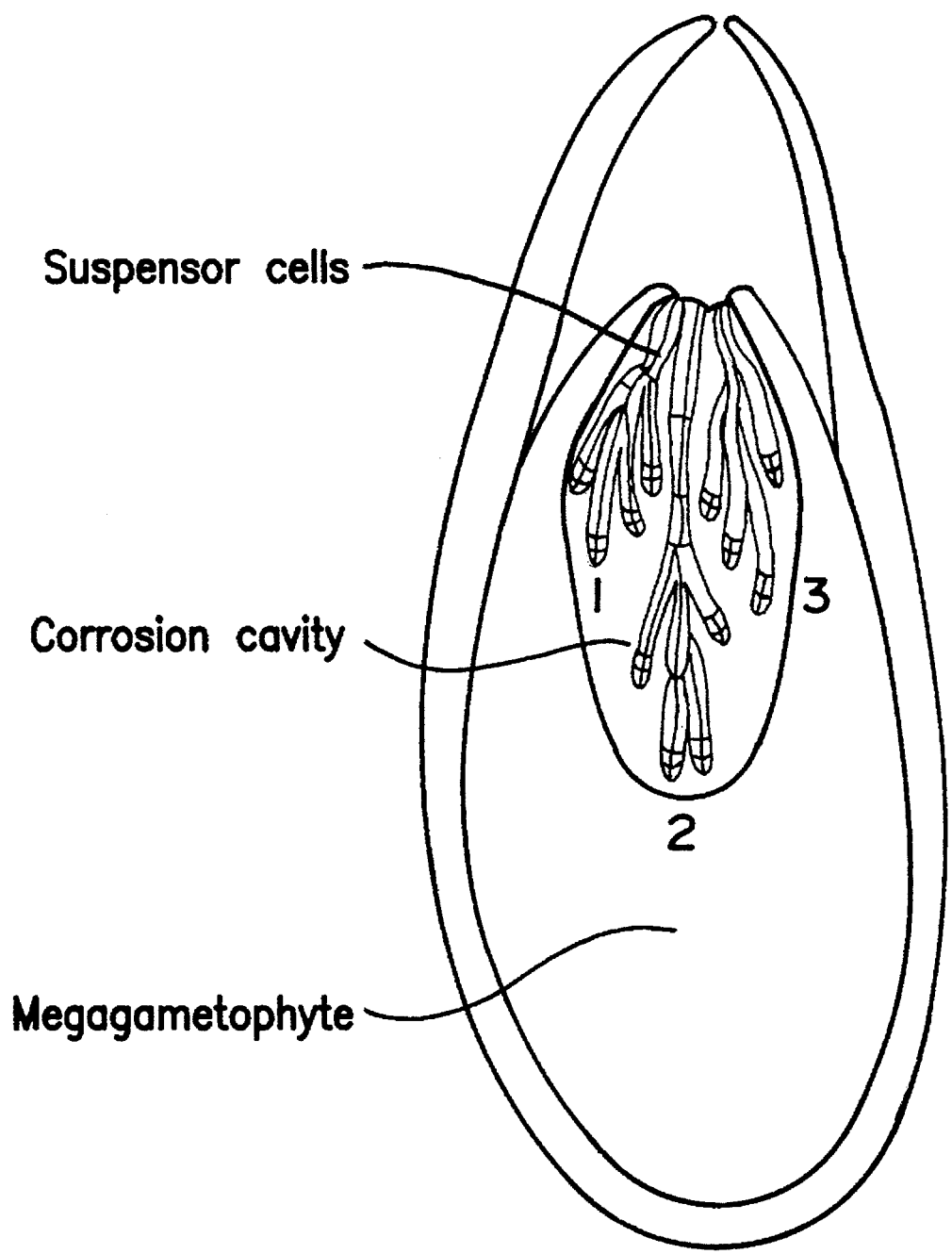
FIG. 3 shows cleavage polyembryony in conifers. Each of the three genetically different zygotic embryos (genotypes 1, 2, and 3) cleaves four ways, resulting in a total of 12 individual embryos. Elongation of suspensor cells pushes the multiple embryos into the corrosion cavity of the megagametophyte. In the figure: A designates suspensor cells; B designates the corrosion cavity; and C designates the megagametophyte.
Figure 4:
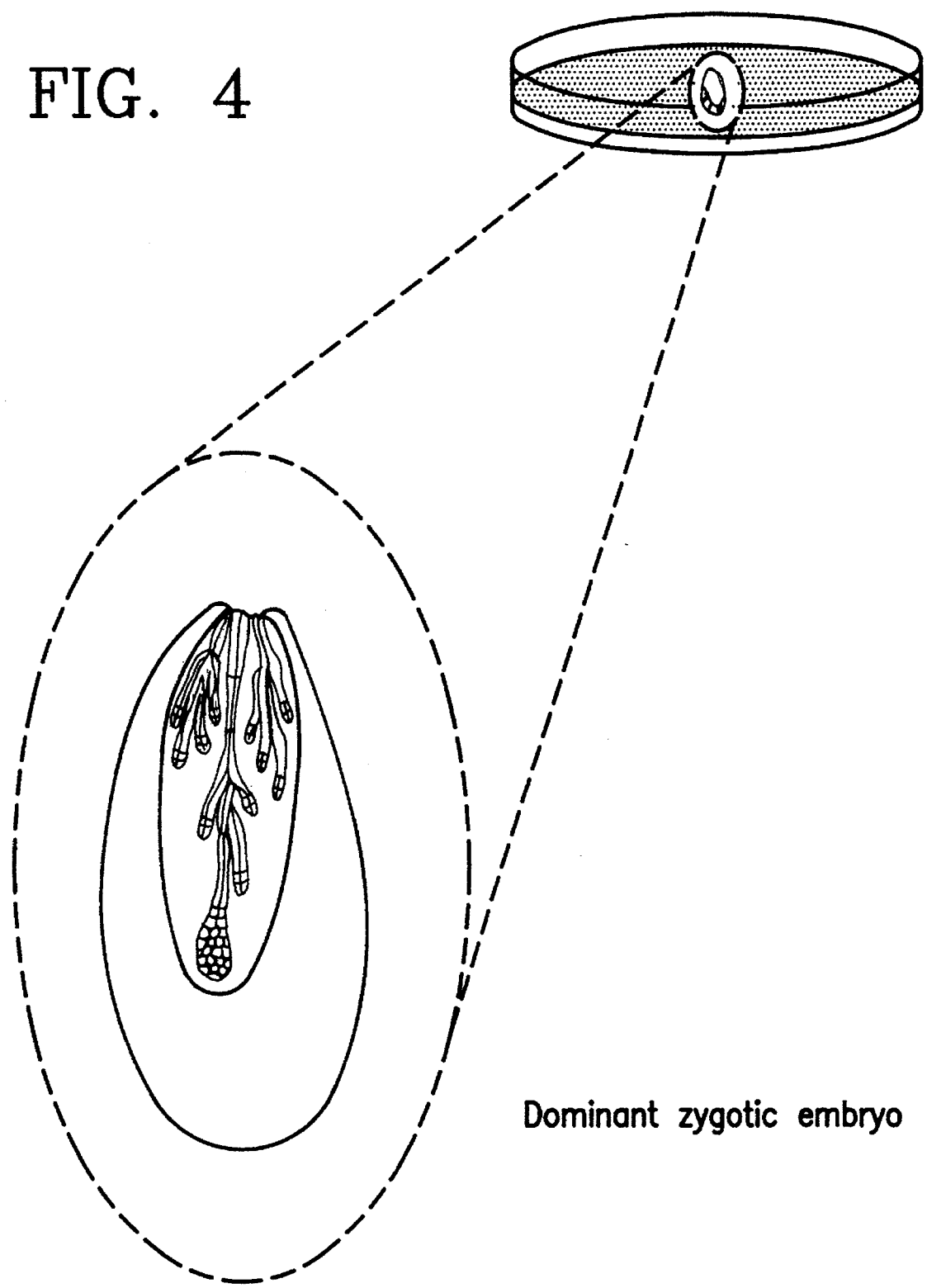
FIG. 4 shows the megagametophyte being cultured. The megagametophyte, which contains the 12 developing zygotic embryos, is cultured in vitro on the surface of nutrient medium. In pines, the optimum time for culture is when one of the zygotic embryos has just commenced enlargement to dominate the other embryos. In the figure A designates the dominant zygotic embryo.

Immature seed cones of loblolly pine (*Pinus taeda* L.) were collected from clone WV42 located in the South Carolina coastal second-generation seed orchard in Ravenel, S.C. The seed cones resulted from controlled pollination with a tri-parental mix of loblolly pollen (FIGS. 1, 2, and 3). The polymix contained freshly collected pollen in a 1:1:1 ratio from the following loblolly pine clones: WV44, WV47, and WV48. Hereafter, the pollen parents are referred to as 1, 2, and 3, respectively. The germination levels of 200 pollen grains per clone on agar plates were 88, 94, and 94 percent, respectively. After collection, the seed cones were stored for three to six weeks in plastic bags at 4° C. At weekly intervals the bags were opened and placed at room temperature for three to four hours to allow moisture on the cones to evaporate. Immature seeds were removed from the cones and sterilized in commercial bleach (20% v/v; equivalent to 1.05% sodium hypochlorite) for 15 minutes and rinsed three times with sterile water. Subsequently, the seed coat, nucellus, and megaspore wall tissue were removed to form the megagametophyte explant. The explants (eight per plate) were placed on the culture induction medium surface with their longitudinal axis parallel to the surface of the medium (FIG. 4).

Basal DCR medium (Gupta and Durzan, 1985) supplemented with 3 mg/l 2,4-dichlorophenoxyacetic acid, 0.5 mg/l $N^6$-benzyladenine, 30 g/l sucrose, 2 g/l Gelrite® (a gelling agent manufactured by Schweizerhall, Inc.), 250 mg/l L-glutamine, 0.5 g/l casein enzymatic hydrolysate (Sigma No. C-4523), and 0.5 g/l myo-inositol (Sigma No. 1-5125) was used for both culture initiation (i.e. induction) and maintenance. The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 70° C.) medium. Twenty ml of medium was poured into 100×15 mm sterile Falcon® (manufactured by Becton Dickinson Labware, Lincoln Park, N.J.) plastic petri plates. After each transfer or subculture, the perimeter of each plate was wrapped twice with Parafilm® (manufactured by American Can Co., Greenwich, Conn.).

Figure 5:
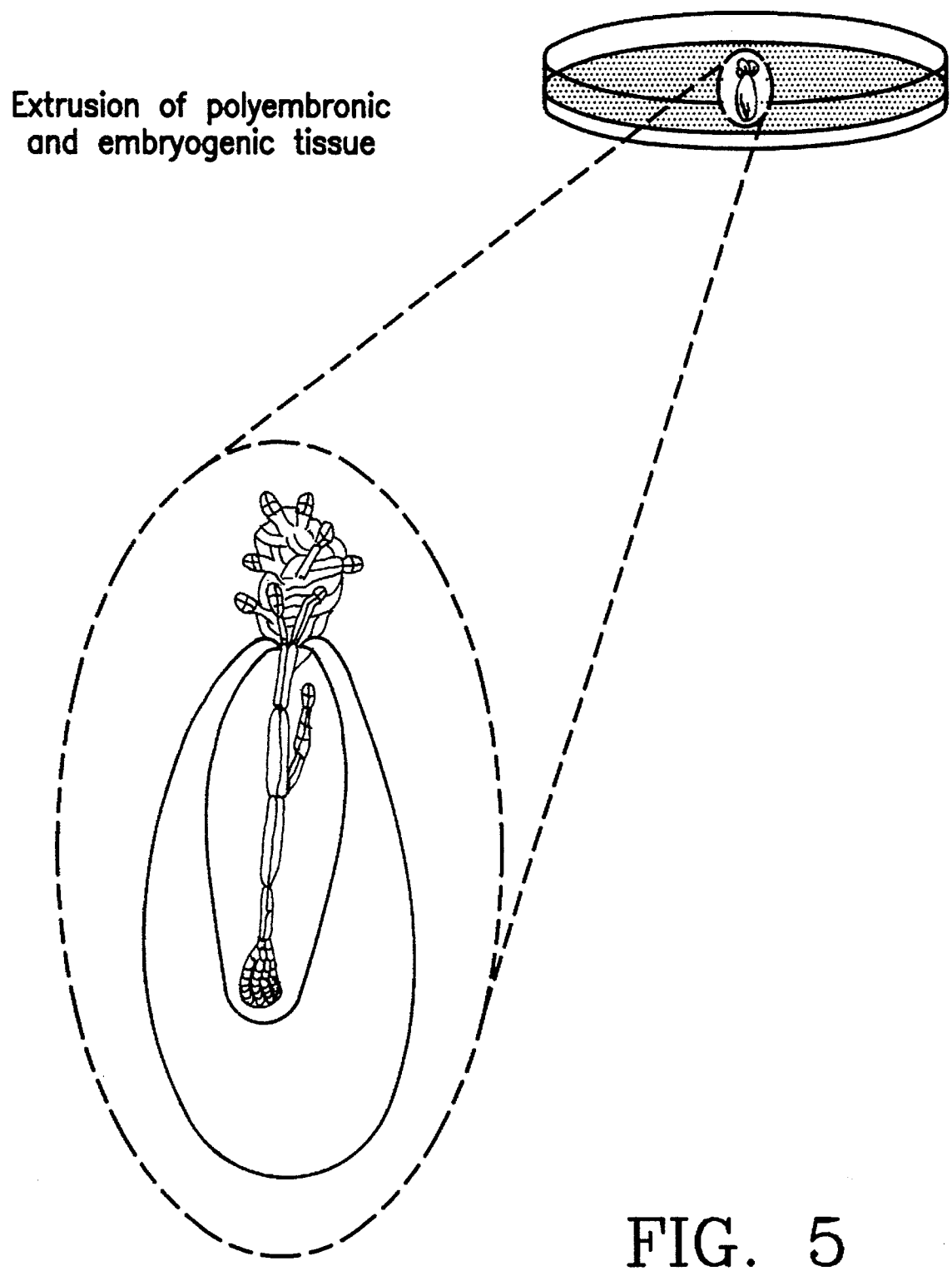
FIG. 5 shows the extrusion of polyembryonic and embryogenic tissue from the megagametophyte. Extrusion of polyembryonic and embryogenic tissue from within the corrosion cavity, through the opening in the micropylar end of the megagametophyte, out onto the nutrient medium. The extruded polyembryonic and embryogenic tissue, in this example, may contain embryos and proliferating cells derived from three different genotypes.
Figure 6:
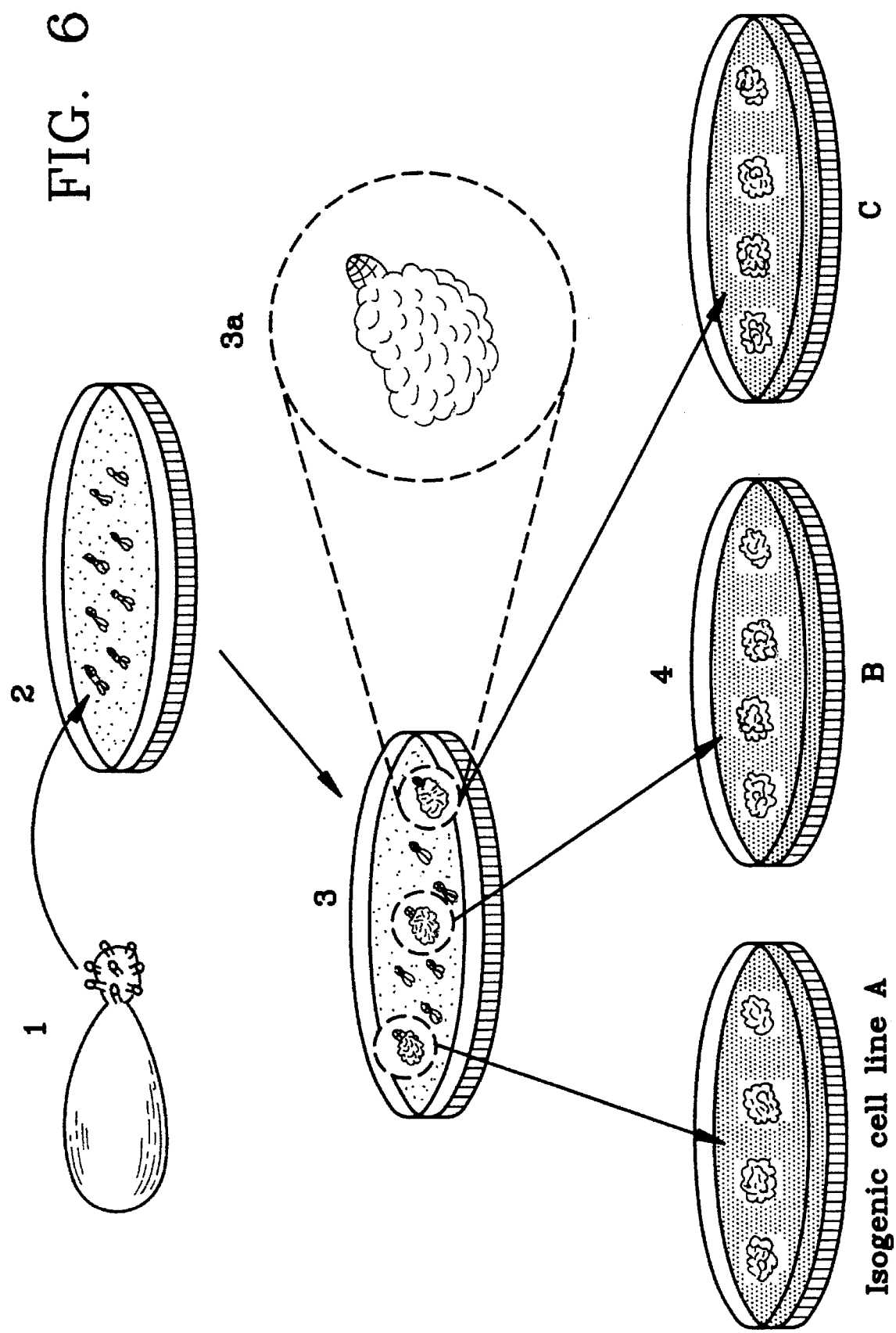
FIG. 6 shows the process for the production of isogenic cell lines. A method for the production of isogenic cell lines derived from polyembryonic and embryogenic tissue extruded from conifer seeds. Step 1: Extrusion of polyembryonic and embryogenic tissue (see FIG. 5). Step 2: Isolation of individual embryos from the extruded tissue and culture of the isolated embryos on an appropriate medium to induce proliferation of embryogenic tissue. Step 3: After 2 to 4 weeks in culture embryogenic tissue proliferates from the responsive individual embryos (3 of 8 embryos, in this example). An expanded view (3a) shows the initial proliferation of embryogenic tissue, derived from cell division in the embryonal and/or suspensor region. Step 4: Establishment of isogenic cell lines (A, B, and C in this example) from each proliferating isolated embryo. The cell lines can be bulked-up for somatic embryo production and plant regeneration via somatic embryogenesis. With the use of genetic markers each cell line can be genotyped to determine if they are genetically different from each other.

Cultures were maintained as 23° C. in the dark for a period of 2 to 4 weeks. The length of time depended on the particular genotype and culture conditions. At the end of this time, a number of explants had each extruded a tissue mass containing zygotic embryos and/or other embryogenic tissues (FIG. 5). Individual embryos were isolated and separated from the extruded tissues by the use of forceps. Forceps were also used to subsequently transfer these isolated individual embryos to a new culture plate containing the same medium previously cited (FIG. 6). This process is depicted in the FIG. 6 diagram as "step 2". Isolated individual embryos were placed on a plate at a distance of at least 2 cm from each other to insure that subsequent cell proliferation from different isolated embryos would not become mixed. After 2 to 4 weeks, responsive isolated embryos had formed embryogenic tissue ("step 3" of FIG. 6). An expanded view of this initial proliferation of embryogenic tissue from the isolated embryos is shown in FIG. 6, part 3a. Thereafter, individual isogenic cell lines derived from individual embryos were coded A, B, C, etc. and were maintained by subculturing (e.g., transferring sectors of the proliferating embryogenic tissue) at 2 to 3 week intervals to a new plate containing the same medium as previously listed. By this method several isogenic cell lines derived from individual seeds of Pinus taeda were established from an individual seed of Pinus taeda (three cell lines are depicted in "step 4" of FIG. 6). Cultures derived from an individual seed were given a seed identification number (e.g., 53), in addition to the cell line code (A, B, and C, etc.) for multiple isogenic cell lines from within a single seed. Thus, cell lines 53A, 53B, and 53C all were derived from individual embryos of seed number 53 (see Table IV). The cell lines were thereafter bulked-up over time for production of somatic embryos and plant regeneration and for genetic analysis (genotyping).

EXAMPLE 2

Following the procedure taught in Example 1, immature seed cones of loblolly pine (Pinus taeda L.) were collected from clone WV42 located in the South Carolina coastal second-generation seed orchard in Ravenel, S.C. The seed cones resulted from controlled pollination with a tri-parental mix of loblolly pollen (FIGS. 1, 2, and 3). The polymix contained freshly collected pollen in a 1:1:1 ratio from the following loblolly pine clones: WV44, WV47, and WV48. Hereafter, the pollen parents are referred to as 1, 2, and 3, respectively. The germination levels of 200 pollen grains per clone on agar plates were 88, 94, and 94 percent, respectively. After collection, the seed cones were stored for three to six weeks in plastic bags at 4° C. At weekly intervals the bags were opened and placed at room temperature for three to four hours to allow moisture on the cones to evaporate. Immature seeds were removed from the cones and sterilized in commercial bleach (20% v/v; equivalent to 1.05% sodium hypochlorite) for 15 minutes and rinsed three times with sterile water. Subsequently, the seed coat, nucellus, and megaspore wall tissue were removed to form the megagametophyte explant. The explants (eight per plate) were placed on the culture induction medium surface with their longitudinal axis parallel to the surface of the medium (FIG. 4).

Basal DCR medium (Gupta and Durzan, 1985) supplemented with 3 mg/l 2,4-dichlorophenoxyacetic acid, 0.5 mg/l $N^6$-benzyladenine, 30 g/l sucrose, 2 g/l Gelrite®, 250 mg/l L-glutamine, 0.5 g/l casein enzymatic hydrolysate (Sigma No. C-4523), and 0.5 g/l myo-inositol (Sigma No. I-5125) was used for both culture initiation (i.e. induction) and maintenance. The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 70° C.) medium. Twenty ml of medium was poured into 100×15 mm sterile Falcon® plastic petri plates. After each transfer or subculture, the perimeter of each plate was wrapped twice with Parafilm®.

Cultures were maintained at 23° C. in the dark for a period of two to four weeks. The length of time depended on the culture conditions and particular genotype being used. At the end of this time the extruded embryogenic tissue (FIGS. 5 and 6) was removed from each responsive explant and transferred using forceps to new medium in one of the following three ways: 1) the entire mass of extruded embryogenic tissue was transferred, 2) small sectors of embryogenic tissue which contained masses of proliferating embryos were removed from the extruded tissue and transferred, or 3) individual embryos were removed from the extruded mass of embryogenic tissue and transferred. Thereafter, cultures were subcultured every 2–3 weeks and maintained as lines derived from individual explants according to the method of initial transfer listed above. That is, lines derived for the entire original mass of embryogenic tissue were coded M, lines from the sectors of embryogenic tissue were coded $S_1$, $S_2$, $S_3$, etc., and lines from individual embryos were coded A, B, C, etc.

The paternal genotypes of embryogenic tissues and mature zygotic embryos were determined with starch gel electrophoresis according to known methods described in Conkle et al., 1982. Tissue samples (about 50 mg of embryogenic tissue or one mature zygotic embryo) were placed in 0.5 ml microcentrifuge tubes, macerated in a 0.2M phosphate extraction buffer (pH 7.5), and centrifuged at 14,000 rpm for eight minutes at 4° C. The supernatant was absorbed until fully saturated onto 2 mm×10 mm wicks cut from Whatman 3 MM chromatography paper. Wicks from each tissue sample were inserted into the origin slit of gels solidified with 12.5% hydrolyzed potato starch (Sigma No. S-4501). A morpholine citrate (pH 6.1) gel and electrode buffer system (Conkle et al., 1982) was run at 45 milliamps constant current for five hours at 4° C. Separate slices of each gel were stained to detect migrational differences in the banding patterns of aconitase (ACO; EC 4.2.1.3), malic dehydrogenase (MDH; EC 1.1.1.37), shikimate dehydrogenase (SKDH; EC 1.1.1.25), and 6-phosphogluconate dehydrogenase (6PGD; EC 1.1.1.44) enzymes.

After two weeks in culture, several explants with extruded embryogenic tissue were fixed in a 1:1:1 solution of formalin: acetic acid: ethanol for histological studies. The fixed megagametopytes were embedded in TissuePrep (Fisher Scientific No. T565), sectioned, and stained with safranin and hematoxylin.

Microscopic sections of megagametophytes, at the time of the initial extrusion of embryogenic tissue, revealed numerous embryos within the corrosion cavity. Some of the embryos were positioned with their apex toward the chalazal end of the megagametophyte; the normal orientation during in situ embryo development in conifer seeds. Other embryos, which were usually smaller embryos, were orientated in the opposite direction, with their apex toward the micropylar end of the megagametophyte. It appeared that these latter embryos were in the process of being extruded from the corrosion cavity through the opening in the micropylar end of the megagametophyte. In addition, other embryos were located outside of the megagametophyte. It was not determined whether the embryos in the extruded tissue were zygotic embryos which had just emerged from the corrosion cavity, or if they were somatic embryos which formed from the zygotic embryos either prior to or just after extrusion. Similarly, in Pinus strobus L., it was not possible to distinguish between the small zygotic embryos and proliferating somatic embryos based on histological evidence (Finer et al., 1989).

Embryogenic tissue that extruded from the micropylar end of megagametophytes of loblolly pine was composed of elongated, translucent suspensor-like cells and numerous opaque embryos with attached suspensor cells. The embryogenic tissue was embedded in a moist, mucilaginous matrix.

Cultures were maintained for 36 (9%) of 392 explants. A total of 70 cell lines were maintained; 27 derived from embryos isolated from the mass of extruded embryogenic tissue, 21 from small sectors of embryogenic tissue, and the remaining 22 from the entire mass of extruded embryogenic tissue.

Embryos isolated from the mass of extruded embryogenic tissue and cultured individually subsequently proliferated to form embryogenic tissue by cell division in the suspensor region. A proliferation of translucent cells preceded the appearance of somatic embryos. Our observations with individual embryos support the hypothesis that cell division and proliferation precedes the formation of somatic embryos in loblolly pine. Conversely, our observations do not support the hypothesis that somatic embryogenesis in loblolly pine results from a direct continuation of the zygotic cleavage process as described for somatic polyembryogenesis (Gupta and Durzan, 1987).

In order to obtain information on the origin of the embryogenic tissue, 15 responsive megagametophytes (e.g., explants from which extruded zygotic embryos and embryogenic tissue had been removed) were longitudinally split open to observe any remaining zygotic embryos in the corrosion cavity (Table I). Ten of the fifteen megagametophytes contained a large zygotic embryo (at or near the stage of cotyledon primordia formation) with intact suspensor cells. The extruded embryogenic tissue did not appear to have originated by proliferation of the suspensor cells at the base of the embryonic region of the large zygotic embryos because the cells in this region were intact and undisturbed. These zygotic embryos were located at the chalazal end of the corrosion cavity; in the position that the dominant zygotic embryo is located during in situ embryo development in Pinus. These observations suggest that the extruded embryogenic tissue of some of the cultures (e.g., from explant Nos. 38, 46, 53, and 60, Table I) originated from the smaller secondary zygotic embryos which were extruded, rather than from the dominant zygotic embryo which remained in the megagametophyte. In contrast, the embryogenic cultures established from explants 47, 49, and 55 may have originated from the dominant zygotic embryo. That is, the dominant zygotic embryo was not found in the corrosion cavity of these explants after extrusion and may have been extruded and subsequently proliferated to form embryogenic tissue. This last observation agreed with the finding that Pinus taeda embryogenic cultures were established from excised (dominant) zygotic embryo (Becwar et al., 1990). Thus, our observations supported the hypothesis that embryogenic cultures of Pinus taeda, in some but not all explants, originated from the smaller secondary zygotic embryos rather than the dominant zygotic embryo.

The paternal origin of the embryogenic tissue samples was determined by the multilocus genotypes at the ACO, MDH1, 6PGD1, and SKDH isozyme loci (Table II). The maternal contribution to the genotype of the tissue sample was fixed because the mother clone is homozygous at the four isozyme loci used in this study. The pollen parent population can contribute a variety of paternally-derived alleles to an embryogenic tissue sample. Examination of paternal alleles or allele combinations shows that they can serve as "markers" for individual pollen parents in this population (Table II). For instance, pollen parent 1 is heterozygous for the ACO allele 5 and homozygous for the SKDH allele 2. Pollen parent 2 is heterozygous for the MDH1 allele 3 and homozygous for 6PGD1 allele 1. Pollen parent 3 is heterozygous for 6PGD1 allele 8. The presence of a marker allele(s) in a sample of embryogenic tissue permits unequivocal identification of the pollen parent(s), and therefore, the culture genotype.

Table I shows a survey of fifteen megagametophyte (MG) explants for the presence of zygotic embryos (ZEs) remaining in the corrosion cavity (CC) after the removal of the extruded embryogenic tissue (ET). The number of culture lines established from each explant is also listed.

TABLE I

| Explant ID No. | Large ZEs at Chalazal End of CC | Small ZEs at Micropylar End of CC | No. of ET Lines Established (Line Code[a]) |
|---|---|---|---|
| 35 | 0 | 0 | 0 |
| 36 | 1 | 0 | 0 |
| 37 | 1 | 0 | 0 |
| 38 | 1 | 0 | 1 (M) |
| 39 | 1 | 1 | 0 |
| 40 | 0 | 0 | 0 |
| 45 | 1 | 0 | 0 |
| 46 | 1 | 0 | 1 (M) |
| 47 | 0 | 0 | 3 ($S_1,S_2,S_3$) |
| 48 | 1 | 0 | 0 |
| 49 | 0 | 2 | 1 (M) |
| 50 | 1 | 0 | 0 |
| 53 | 1 | 1 | 3 (A,D,F) |
| 55 | 0 | 0 | 6 (A,C,D,E,$S_1,S_2$) |
| 60 | 1 | 0 | 4 (A,B,$S_1,S_2$) |

[a]See example 2 for a description of the codes.

Table II shows diploid genotypes of the parental clones at four isozyme loci. Marker alleles for the pollen parent population are underscored.

TABLE II

| | Genotype at Isozyme Locus | | | |
|---|---|---|---|---|
| Parent | ACO | MDH1 | 6PGD1 | SKDH |
| WV44 (pollen 1) | 1<u>5</u> | 11 | 22 | <u>22</u> |
| WV47 (pollen 2) | 11 | 1<u>3</u> | <u>11</u> | 11 |
| WV48 (pollen 3) | 11 | 11 | 2<u>8</u> | 11 |
| WV42 (mother) | 11 | 11 | 22 | 11 |

Preliminary tests showed that the position of marker bands for the four isozyme loci used in this study were equivalent between samples taken from embryogenic tissue and from mature zygotic embryos. We were therefore able to use the known isozyme polymorphisms (Brown and Blush 1989) to genotype the embryogenic cultures.

The isozyme analysis of embryogenic cultures derived from 36 megagametophyte explants showed that three of the explants (Numbers 32, 41, and 47) produced multiple cell lines with genotypic differences among the cell lines (Table IV). In other words, genotypic differences were found between different cell lines derived from zygotic embryos of each megagametophyte explant. We did not find evidence for multiple genotypes (genetic mosaics) within a single cell line. Refer to Table IV for a summary of the paternal genotypes of the embryogenic cultures.

Over half (58%) of the cultures derived from the megagametophyte explants of clone WV42 had pollen 2 as a parent (Table III). In contrast to the higher proportion of pollen parent 2 among the embryogenic cultures, there was a higher proportion (49%) of pollen parent 1 among the surviving zygotic embryos derived from the mature cones of the same controlled pollination. As indicated previously, the viability levels of the three pollens were similar. Therefore, the observed variances in paternity ratios from 1:1:1 in either the embryogenic cultures or the mature zygotic embryos can not be attributed to differences in pollen viability. The difference between the paternity ratios of the embryogenic cultures and the mature embryos suggests that zygotic embryos derived from pollen parent 2 were more competitive in terms of their ability to survive and proliferate in vitro. The differences in paternity ratios also provide indirect evidence that most of the embryogenic cell lines were not derived from the dominant zygotic embryo in each seed. This agrees with the previously mentioned observation that megagametophytes frequently contained a dominant zygotic embryo after the extrusion of zygotic embryos and embryogenic tissue (see Table I) and that the embryogenic tissue did not appear to the derived from the dominant embryo.

Table III shows paternity ratios of embryogenic tissue (ET) and mature zygotic embryos (ZEs) derived from controlled pollination of clone WV42 with a 1:1:1 tri-parental mix of pollens 1, 2, and 3.

TABLE III

| Tissue Sampled | Number of Seeds | Number and (Proportion) of Samples with Pollen Parent | | | Probability[a] |
|---|---|---|---|---|---|
| | | 1 | 2 | 3 | |
| ET[b] | 36 | 11 (.31) | 21 (.58) | 7 (.19) | 0.05 |
| Mature ZEs | 109 | 53 (.49) | 37 (.34) | 19 (.17) | 0.004 |

[a]Probability, using chi-square, that the observed ratio is not significantly different than 1:1:1.
[b]Because three seeds had embryogenic tissue with multiple pollen parents, the total number of samples (39) does not equal the number of seeds sampled (36).

Table IV shows paternal genotypes of seventy loblolly pine embryogenic cell lines as determined by isozyme analysis. The cell lines originated from zygotic embryos derived from mother tree WV42 which was pollinated with a 1:1 mix of pollen from trees WV44, WV47, and WV48. The pollen parents are coded 1, 2, and 3, respectively.

TABLE IV

| Explant Id. Number | Cell Line Code[a] | Isozyme Run Number | | |
|---|---|---|---|---|
| | | a | b | c |
| 4 | M | 1 | 1 | |
| 5 | M | 1 | 1 | |
| 6 | M | 2 | 2*[b] | |
| 7 | M | 1 | 1 | |
| 31 | $S_2$ | 2 | 2 | |
| | $S_3$ | 2 | 2 | |
| | $S_4$ | 2 | 2 | |
| | $S_5$ | 2 | 2 | |
| | A | 2 | 2 | |
| | C | 2 | 2 | |
| | D | 2 | 2 | |
| 32[c] | $S_1$ | 1 | 1 | 1 |
| | A | 3 | not 2 | 3* |
| | C | 1 | 1 | 1 |
| | D | 1 | 1 | 1 |
| 38 | M | 3 | 3* | |
| 41[c] | $S_1$ | not 2 | not 2 | 1* |
| | B | not 2 | not 2 | not 2 |
| | J | 2 | 2 | 2 |
| 42 | M | 3 | 3 | |
| 43 | $S_1$ | 1 | 1 | |
| 44 | $S_1$ | not 2 | 1 | |
| | B | not 2 | 1 | |
| 46 | M | 3 | 3* | |
| 47[c] | $S_1$ | 2 | 2 | |
| | $S_2$ | 1 | 1 | |
| | $S_3$ | 2 | 2 | |
| 49 | M | 2 | 2 | |
| 53 | A | 1 | 1 | |
| | D | 1 | 1 | |
| | F | 1 | | |
| 55 | $S_1$ | 2 | | |
| | $S_2$ | 2 | 2 | |
| | A | 2 | 2 | |
| | C | 2 | 2 | |
| | D | 2 | | |
| | E | 2 | 2 | |
| 57 | $S_1$ | 2 | 2 | |
| | $S_2$ | 2 | 2 | |
| | $S_3$ | 2 | 2 | |
| | B | 2* | 2 | |
| | C | 2 | | |
| | E | 2* | 2 | |
| 59 | A | 3 | 3 | |
| 60 | $S_1$ | 3 | 3* | |
| | $S_2$ | 3 | 3 | |
| | A | 3 | 3 | |
| | B | 3 | 3 | |
| 61 | M | 2 | 2 | |
| 62 | M | 2 | 2 | |
| 63 | M | 2* | 2 | |
| 64 | M | 2 | 2 | |
| 66 | M | 2 | 2 | |
| 68 | M | 2 | 2 | |
| 69 | M | 2* | 2 | |
| 70 | $S_1$ | 2 | 2 | |
| | $S_2$ | 2 | 2 | |
| | A | 2 | 2 | |
| 72 | M | 2 | 2 | |
| 75 | M | 2 | 2 | |
| 78 | $S_1$ | 2 | 2 | |
| | A | 2 | 2 | |
| | B | 2 | 2 | |
| | C | 2 | 2 | |
| 84 | M | 2 | 2 | |
| 94 | D | 1 | | |
| 95 | M | 2* | 2* | |
| 97 | M | 3 | 3 | |
| 98 | M | 1 | 1 | |
| 99 | M | 2* | 2 | |

[a]See example 2 for a description of the codes.
[b]An * indicates the marker band was faint.
[c]Explants which had cell lines with different pollen parents.

As Table IV shows, the cell lines derived from explants numbers 32, 41, and 47 were not all genetically identical (i.e., they were derived from different zygotic embryos formed as a result of simple polyembryony). This result illustrates that genetically different cell lines can be derived from an individual conifer seed. Also, no evidence was found for multiple genotypes within individual cell lines— indicating that all the isolated cell lines were isogenic.

It will be understood that many variations can be made in the procedures described for the various culturing stages while still retaining the necessary and critical isolation of individual embryos immediately after their extrusion from the megagametophyte. It is the intention of the inventors that such variations should be included within the scope of their invention if found defined within the following claims.

BIBLIOGRAPHY

Allen, G. S. and J. N. Owens, 1972; *The Life History of Douglas Fir.* Published by Information Canada, Ottawa.

Attree, S. M., T. E. Tautorus, D. I. Dunstan, and L. C. Fowke, 1991; Somatic embryo maturation, germination, and soil establishment of plants of black and white spruce (*Picea mariana* and *Picea glauca*). *Canadian Journal Bot.* 68:2583–2589.

Becwar, M. R., S. R. Wann, M. A. Johnson, V. A. Verhagan, R. P. Feirer, and R. Nagmani, 1988; Development and characterization of in vitro embryogenic systems in conifers. In: Ahuja MR (ed) *Somatic Cell Genetics of Woody Plants.* Kluwer Academic Publ, Dordrecht, The Netherlands 1–18.

Becwar, M. R., R. Nagmani, and S. R. Wann, 1990; Initiation of embryogenic cultures and somatic embryo development in loblolly pine (*Pinus taeda* L.). *Canadian Journal Forest Research* 20:810–817.

Collins, G. B. and J. W. Grosser, 1984; Culture of embryos. In: *Cell Culture and Somatic cell Genetics of Plants*, Vol 1, Laboratory procedures and their application. (I. K. Vasil, ed.). Academic Press, New York.

Conkle, M. T., P. D. Hodgskiss, L. B. Nunnally, and S. C. hunter, 1982; Starch gel electrophoresis of conifer seeds: A laboratory manual. *USDA Forest Service General Technical Report PSW-64.* Pacific Southwest Forest and Range Experiment Station, Berkeley, Calif.

Durzan, D. J. and Gupta, P. K., 1987; Somatic embryogenesis and polyembryogenesis in Douglas-fir cell suspension cultures. *Plant Science.* 52:229–235.

Finer, J. J., H. B. Kriebel, and M. R. Becwar, 1989; Initiation of embryogenic callus and suspension cultures of eastern white pine (*Pinus strobus* L.). *Plant Cell Reports* 8:203–206.

Gupta, P. K. and D. J. Durzan, 1985; Shoot multiplication from mature trees of Douglas-fir (*Pseudotsuga menziesii*) and sugar pine (*Pinus lambertiana*). *Plant Cell Reports* 4:177–179.

Gupta, P. K. and D. J. Durzan, 1986; Somatic polyembryogenesis from callus of mature sugar pine embryos. *Bio/Technology* 4:643–645.

Gupta, P. K. and D. J. Durzan, 1987; Biotechnology of somatic polyembryogenesis and plantlet regeneration in loblolly pine. *Bio/Technology* 5:147–151.

Klimaszewska, K., 1989; Plantlet development from immature zygotic embryos of hybrid larch through somatic embryogenesis. *Plant Science* 63:95–103.

Murashige, T. and F. Skoog, 1962; A revised medium for rapid growth and bioassays with tobacco tissue cultures. *Physiologia Plantarum* 15: 473–493.

Norgaard, J. V. and P. Krogstrup, 1991; Cytokinin induced somatic embryogenesis from immature embryos of *Abies nordmanniana* Lk. *Plant Cell Reports* 9:509–513.

Schuller, A., G. Reuther, and T. Geier, 1989; Somatic embryogenesis from seed explants of *Abies alba*. *Plant Cell Tissue and Organ Culture* 17:53–58.

Singh, H., 1978; *Embryology of Gymnosperms.* Gebruder Borntraeger, Berlin-Stuttgart.

What is claimed is:

1. A process for the production of isogenic cell lines from conifers, comprising:

(a) dissecting an immature conifer seed and removing zygotic embryo-containing megagametophyte, (b) placing said megagametophyte on a culture induction medium for 4 to 56 days to induce extrusion of embryogenic tissue comprising zygotic embryos, (c) isolating and extracting the individual embryos from the extruded tissue, and (d) transferring said isolated individual embryos to appropriate culture induction medium to permit the individual cell lines to proliferate.

2. The process of claim 1 wherein the immature conifer seed is selected from the conifer genera group consisting of Abies, Chamaecyparis, Cupressus, Juniperus, Larix, Libocedrus, Picea, Pinus, Pseudotsuga, Sequoia, Taxus, Taxodium, Thuja, Torreya, and Tsuga.

3. The process of claim 1 wherein the period of time allowed for inducement of the extrusion of said embryogenic tissue is 14 to 28 days.

4. The process of claim 1 which further comprises genotyping the isogenic cell lines via genetic markers.

5. The process of claim 1 which further comprises genotyping the isogenic cell lines via DNA markers.

6. The process of claim 1 which further comprises genotyping the isogenic cell lines via protein markers.

7. The process of claim 1 which further comprises genotyping the isogenic cell lines via isozyme markers.

8. The process of claim 1 which further comprises genotyping the isogenic cell lines via morphological markers.

* * * * *

UNITED STATES PATENT AND TRADEMARK OFFICE
CERTIFICATE OF CORRECTION

PATENT NO. : 5,610,051                                              Page 1 of 4
DATED     : March 11, 1997
INVENTOR(S) : Michael R. Becwar and Thomas D. Blush It is certified that error appears in the above-indentified patent and that said Letters Patent is hereby corrected as shown below:

On the Title page, item [56], References Cited, please insert: --

Atree, S. M., T. E. Tautorus, D. I. Dunstan, and L. C. Fowke, 1991; Somatic embryo maturation, germination, and soil establishment of plants of black and white spruce (*Picea mariana* and *Picea glauca*). Canadian Journal Bot. 68:2583-2589.

Becwar, M. R., S. R. Wann, M. A. Johnson, V. A. Verhagen, R. P. Feirer, and R. Nagmani, 1988; Development and characterization of *in vitro* embryogenic systems in conifers. In: Ahuja MR (ed) Somatic Cell Genetics of Woody Plants. Kluwer Academic Publ, Dordrecht, The Netherlands 1-18.

Becwar, M. R., R. Nagmani, and S. R. Wann, 1990; Initiation of embryogenic cultures and somatic embryo development in loblolly pine (*Pinus taeda L.*). Canadian Journal Forest Research 20:810-817.

Collins, G. B. and J. W. Grosser, 1984; Culture of embryos. In: Cell Culture and Somatic Cell Genetics of of Plants, Vol. 1, Laboratory procedures and their application. (I. K. Vasil, ed.). Academic Press, New York.

UNITED STATES PATENT AND TRADEMARK OFFICE
CERTIFICATE OF CORRECTION

PATENT NO.  : 5,610,051
DATED       : March 11, 1997
INVENTOR(S) : Michael R. Becwar and Thomas D. Blush It is certified that error appears in the above-indentified patent and that said Letters Patent is hereby corrected as shown below:

Conkle, M. T., P. D. Hodgskiss, L. B. Nunnally, and S. C. Hunter, 1982; Starch gel electrophoresis of conifer seeds: A laboratory manual. USDA Forest Service General Technical Report PSW-64. Pacific Southwest Forest and Range Experiment Station, Berekeley, Calif.

Durzan, D. J. and Gupta, P. K., 1987; Somatic embryogenesis and polyembryogenesis in Douglas-fir cell suspension cultures. Plant Science. 52:229-235.

Finer, J. J., H. B. Kriebel, and M. R. Becwar, 1989; Initiation of embryogenic callus and suspension cultures of eastern white pine (Pinus strobus L.). Plant Cell Reports 8:203-206.

Gupta, P. K. and D. J. Durzan, 1985; Shoot multiplication from mature trees of Douglas-fir (Pseudotsuga menziesii) and sugar pine (Pinus lambertiana). Plant Cell Reports 4:177-179.

Gupta, P. K. and D. J. Durzan, 1986; Somatic polyembryogenesis from callus of mature sugar pine embryos. Bio/Technology 4:643-645.

UNITED STATES PATENT AND TRADEMARK OFFICE
CERTIFICATE OF CORRECTION

PATENT NO. : 5,610,051

DATED : March 11, 1997

INVENTOR(S) : Michael R. Becwar and Thomas D. Blush

It is certified that error appears in the above-indentified patent and that said Letters Patent is hereby corrected as shown below:

Gupta, P. K. and D. J. Durzan, 1987; Biotechnology of somatic polyembryogenesis and plantlet regeneration in loblolly pine. Bio/Technology 5:147-151.

Klimaszewska, K., 1989; Plantlet development from immature zygotic embryos of hybrid larch through somatic embryogenesis. Plant Science 63:95-103.

Murashige, T. and F. Skoog, 1962; A revised medium for rapid growth and bioassays with tobacco tissue cultures. Physiologia Plantarum 15: 473-493.

Norgaard, J. V. and P. Krogstrup, 1991; Cytokinin induced somatic embryogenesis from immature embryos of Abies nordmanniana Lk. Plant Cell Reports 9:509-513.

Schuller, A., G. Reuther, and T. Geier, 1989; Somatic embyrogenesis from seed explants of Abies alba. Plant Cell Tissue and Organ Culture 17:53-58.

--.

UNITED STATES PATENT AND TRADEMARK OFFICE
CERTIFICATE OF CORRECTION

PATENT NO. : 5,610,051
DATED : March 11, 1997
INVENTOR(S) : Michael R. Becwar and Thomas D. Blush It is certified that error appears in the above-indentified patent and that said Letters Patent is hereby corrected as shown below:

In column 13, line 22, delete the first "the" and insert therefor --be--.

In column 13, line 46, delete "1:1" and insert therefor --1:1:1--.

In columns 13 and 14, Table IV, immediately following the table header, flush right, insert -- ---pollen parent--- --.

Signed and Sealed this

Second Day of September, 1997

BRUCE LEHMAN

Attest:

Attesting Officer

Commissioner of Patents and Trademarks